United States Patent [19]

Maier

[11] 4,351,779
[45] Sep. 28, 1982

[54] PROCESS FOR THE PRODUCTION OF METHYLAMINOMETHYLPHOSPHONIC ACID ESTERS

[75] Inventor: Ludwig Maier, Arlesheim, Switzerland

[73] Assignee: Ciba-Geigy Corporation, Ardsley, N.Y.

[21] Appl. No.: 182,170

[22] Filed: Aug. 28, 1980

Related U.S. Application Data

[60] Continuation-in-part of Ser. No. 102,463, Dec. 10, 1979, abandoned, which is a division of Ser. No. 947,271, Sep. 29, 1978, abandoned.

[30] Foreign Application Priority Data

Oct. 4, 1977 [CH] Switzerland ................ 12100/77
Oct. 3, 1978 [GB] United Kingdom .......... 39087/78

[51] Int. Cl.³ ............................................. C07F 9/40
[52] U.S. Cl. .......................... 260/970; 260/502.5 R; 260/944
[58] Field of Search ....................................... 260/970

[56] References Cited

U.S. PATENT DOCUMENTS 4,104,050  8/1978  Dutra ............................... 260/944

FOREIGN PATENT DOCUMENTS 123529  1/1977  German Democratic Rep. ................................. 260/970

OTHER PUBLICATIONS

Kosdapoff et al., "Organic Phosphorus Compounds", vol. 7, (1977), pp. 10 & 11.

Primary Examiner—Anton H. Sutto
Attorney, Agent, or Firm—Frederick H. Rabin

[57] ABSTRACT

A process for the production of methylaminomethylphosphonic acid and its esters is disclosed. It comprises heating trimethylhexahydro-s-triazine with at least 3 moles of a sterically hindered secondary phosphite and if desired converting the resulting diester or salt thereof into a corresponding hemiester or the free methylaminomethylphosphonic acid.

5 Claims, No Drawings

PROCESS FOR THE PRODUCTION OF METHYLAMINOMETHYLPHOSPHONIC ACID ESTERS

CROSS REFERENCE TO RELATED APPLICATIONS

This is a continuation-in-part of my application Ser. No. 102,463 filed on Dec. 10, 1979, which is a division of my application Ser. No. 947,271 filed on Sept. 29, 1978, both now abandoned.

DETAILED DISCLOSURE

The present invention provides a novel process for the production of methylaminomethylphosphonic acid esters and of the free acid itself.

The known methylaminomethylphosphonic acid of the formula I

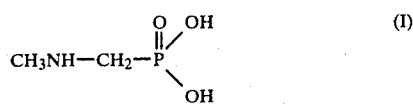

has interesting herbicidal properties which lend added importance to this compound. Up till now, it has only been possible to prepare this known compound by relatively complicated methods.

According to the teaching of U.S. Pat. No. 2,328,358, the N-methyl-N-hydroxymethylstearamide of the formula

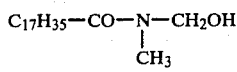

is reacted with $PCl_3$ to give the corresponding phosphonic dichloride, which, after treatment with dilute hydrochloric acid, affords the corresponding aminophosphonic acid

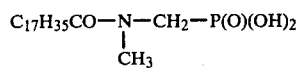

which is then saponified to produce the methylaminomethylphosphonic acid.

The very lengthy reaction times constitute a severe drawback of this process.

In another known process (disclosed in U.S. Pat. No. 3,907,652), the N-tertiary aminomethylphosphonic acid of the formula

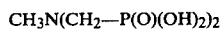

is prepared initially by a Mannich reaction of methylamine, formaldehyde and phosphorous acid ($H_3PO_3$) [Journ. Org. Chem. 31, 1603 (1966)] and subsequently oxidised by electrolysis to $CH_3NH—CH_2—P(O)(OH)_2$ with removal of a phosphonomethyl group.

In 1952, E. K. Fields published a general method for the production of dialkylaminomethylphosphonic acid esters by reaction of aldehydes or ketones with primary or secondary amines and diesters of phosphorous acid (secondary phosphites) [Am. Soc. 74, 1528 (1952)]. It is stated in this publication that the reaction is of general application for aldehydes and ketones, but that primary amines afford substantially poorer yields because of secondary reactions. Finally, Fields expressly declares in his paper that the reaction is only possible with secondary amines or primary alkylamines containing tertiary alkyl groups when using formaldehyde, as the formaldimine intermediates formed from formaldehyde and other primary alkylamines (having no tertiary alkyl groups) polymerise too rapidly. This fact is also apparent from Houben-Weyl, Methoden der organ. Chemie, Vol. XI/2, page 78 (1958).

The "trimeric" hexahydro-s-triazines of the type

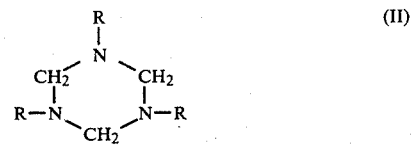

wherein R represents an unsubstituted or substituted alkyl, cycloalkyl or benzyl radical, can be considered as partially polymerised formaldimine intermediates.

Reactions of such N-substituted hexahydro-s-triazine derivatives of the formula II with secondary phosphites have been described in the more recent literature. These references relate to reactions of hexahydrotriazines of the formula (II), wherein R is a higher radical, such as benzyl, with diethylphosphite [Tetrahedron Letters 46, page 4645 (1973)], and to reactions of hexahydrotriazines of the formula (II), wherein R is an alkyl radical of 3 or 4 carbon atoms, with dialkylphosphites (German Democratic Republic Patent Specification 123,529) and distillation of the esters to give relatively poor yields.

This reaction cannot be generally employed and cannot be carried out using trimethylhexahydro-s-triazine as starting material. The reaction of $(CH_3—N—CH_2)_3$ with dimethyl phosphite is so vigorous that it is completely uncontrollable, whereas the reaction of $(CH_3—N—CH_2)_3$ with diethyl phosphite and other straight-chain lower dialkyl phosphites results in resinification of the reaction mixture. This is probably the reason why this reaction with $C_1$-$C_2$trialkylhexahydro-s-triazines is nowhere described in the literature.

Surprisingly, it has now been found that it is possible to avoid these difficulties and to carry out the reaction of trimethylhexahydro-s-triazines with secondary phosphites to produce esters of methylaminomethylphosphonic acid in good yield by using a sterically hindered secondary phosphite, such as a dialkyl phosphite having branched alkyl groups, or a cyclic secondary phosphite, and precipitating the resulting ester with hydrohalic acid, especially hydrochloric acid, in the form of a halide (hydrochloride), thereby avoiding distillation of the unstable ester.

The process of the present invention for the production of methylaminomethylphosphonic acid esters and of the free acid based thereon comprises heating trimethylhexahydro-s-triazine of the formula

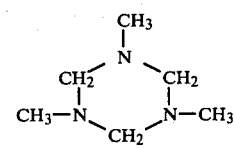

with at least 3 moles of a sterically hindered secondary phosphite, precipitating the resulting diester, dissolved in an organic solvent, in the form of a hydrohalide by introducing hydrohalic acid, and, if desired, converting this ester into a corresponding hemiester and/or the free methylaminomethylphosphonic acid.

By a sterically hindered secondary phosphite is meant, on the one hand, a dialkyl phosphite having branched alkyl radicals, for example diisopropyl phosphite, di-tert-butyl phosphite, diisobutyl phosphite etc., and, on the other, a cyclic phosphite, in particular 5,5-dimethyl-[1,3,2]-dioxaphosphorinane of the formula

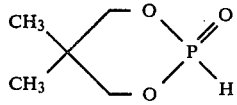

The reaction of such sterically hindered phosphites with trimethylhexahydro-s-triazine proceeds normally and under control at temperatures between about 20° and 150° C. and the reaction mixture does not resinify. Preferably, the temperature is between 50° and 120° C., more preferably from 100° C. to 110° C. The choice of sterically hindered phosphites as reactants has made it possible for the first time to produce esters of methylaminomethylphosphonic acid in this manner.

The resulting esters are unstable and partially decompose during vacuum distillation. A further advantage of the process of the invention resides in the precipitation of the diesters from an organic, especially ethereal, solution by introducing preferably gaseous hydrochloric acid, to produce the hydrochloride of the ester.

The hydrochlorides of the esters can be readily hydrolysed to the free methylaminomethylphosphonic acid, for example with concentrated hydrochloric acid under reflux conditions.

Surprisingly, however, these diesters can also be converted stepwise into the free methylaminomethylphosphonic acid by thermal decomposition (pyrolysis) via the isolatable intermediate of the corresponding hemiester. In practice, this thermal decomposition is carried out by heating the precipitated diester hydrochloride for some time (10 to 20 hours) to about 170° C., whereby an ester radical is removed and the hemiester is formed. This latter can be pyrolysed by further heating to a higher temperature, such as 230°–240° C., to produce the free methylaminomethylphosphonic acid.

The following Examples illustrate the process of the invention in more detail.

EXAMPLE 1

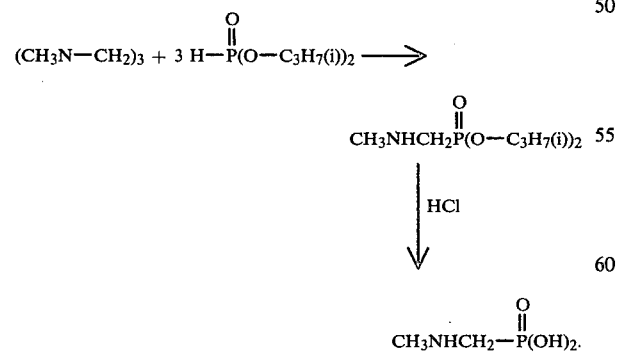

To 8.61 g (0.067 mole) of commercially available trimethylhexahydro-s-triazine (prepared from formaldehyde and methylamine in the presence of sodium hydroxide solution) are added 33.23 g (0.2 mole=3 times the molar amount) of diisopropyl phosphite and the mixture is heated, with stirring, to 100°–110° C. for 4 hours. Then diethyl ether is added and the diisopropyl ester of methylaminomethylphosphonic acid is precipitated in the form of its hydrochloride by introducing gaseous HCl, affording 35.7 g (72.6%) of the diester hydrochloride with a melting point of 128°–131° C. (with decomp.).

The NMR spectrum of this diester hydrochloride confirms its structure.

$^1$H—NMR (in dimethyl sulfoxide) (CH$_3$)=1.45 ppm (d, J$_H$ 6 Hz 12H); N—CH$_3$ 2.73 ppm (s, 3H); P—CH$_2$ 3.55 ppm (d, J$_{PCH}$ 13 Hz, 2H); O—CH 4.83 ppm (2 septets, 2H); NH.HCl 8.5 ppm.

Saponification is carried out by heating a solution of 12.3 g of the diester hydrochloride in 100 ml of conc. hydrochloric acid for 20 hours under reflux and then concentrating the reaction mixture to dryness. The oily residue is recrystallised from water/ethanol, affording 3.60 g (57.6%) of pure methylaminomethylphosphonic acid with a melting point of 265°–270° C.

EXAMPLE 2

A mixture of 830 g (5 moles) of diisopropyl phosphite and 213 g (1.67 moles) of trimethylhexahydro-s-triazine is stirred for 16 hours at 110° C. The resulting diester is not precipitated with HCl as in Example 1, but subjected to fractional distillation. In addition to first runnings and a substantial amount of residue in the flask, only 290.3 g of CH$_3$NHCH$_2$P(O)(O—iC$_3$H$_7$)$_2$ with a boiling point of 72°–75° C./0.45 torr are obtained, corresponding to a yield of 28%. The substance decomposed partially during the distillation, for which reason it is more advantageous to isolate the ester in the form of the hydrochloride as in Example 1.

The NMR spectrum of the distilled diisopropyl ester of methylaminomethylphosphonic acid corresponds to its structure.

Analysis: C$_8$H$_{20}$NO$_3$P (209.23): calculated: C 45.93 H 9.64 N 6.70 P 14.81%. found: C 45.97 H 9.52 N 6.80 P 14.43%.

EXAMPLE 3

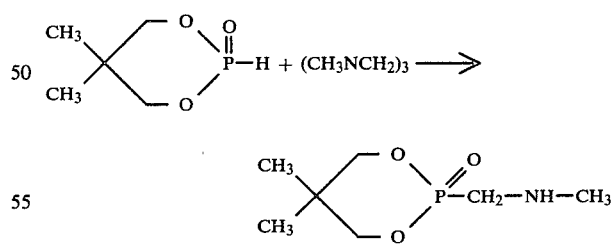

A mixture of 46 g (0.31 mole) of 5,5-dimethyl-[1,3,2]-dioxaphosphorinane (Organic Phosphorus Compounds, ed. G. M. Kosolapoff and L. Maier, John Wiley & Sons, New York, Vol. 5, page 208 (1973) and 13 g (0.1 mole) of trimethylhexahydro-s-triazine is heated, with stirring, to 110° C. for 2 hours and then allowed to stand for 21 hours at room temperature.

Fractional distillation yields 24 g (42%) of the final product (cyclic ester) as a colourless viscous oil with a boiling point of 135°–140° C./0.1 torr.

Analysis: $C_7H_{16}NO_3P$ (193.18): calculated: C 43.52 H 8.35 N 7.25 P 16.03%. found: C 44.17 H 8.79 N 6.72 P 15.00%.

$^1$H—NMR (in $CDCl_3$) $CH_3$ 0.91 and 1.12 ppm (S, 6H); NH 1.78 ppm, 1H; $NCH_3$ 2.43 ppm (d $J_{NHCH}$ 1.5 Hz) 3H; $PCH_2$ 3.0 ppm (d $J_{PCH}$ 12 Hz, 2H); $OCH_2$ 4.0 ppm (m), 4H.

EXAMPLE 4

The hydrochloride of the diisopropyl ester of methylaminomethylphosphonic acid obtained in Example 1 was pyrolysed stepwise to give the free acid as follows: 12.2 g of

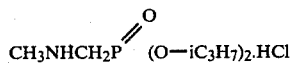

are heated in an oil bath for 14 hours to 170° C., leaving as residue 9.3 g (91.4%) of the hemiester hydrochloride

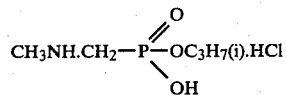

Melting point: 220°–223° C. (with decomp.)

4.1 g of this hemiester hydrochloride are heated for 3 hours to 230°–240° C. in an oil bath, yielding a slightly yellowish brittle substance which is recrystallised from water/ethanol. Yield: 2.7 g (97.5%) of the free acid

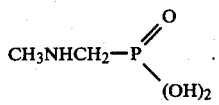

The diesters and hemiesters (monoesters) obtained by the process of the present invention are novel compounds which, like the free acid, are herbicidally active and can be used as herbicidal active compounds and as constituents of herbicidal compositions.

What is claimed is:

1. A process for the production of methylaminomethylphosphonic acid esters and of the corresponding free acid, which comprises heating at a temperature of from about 20° to about 150° C., trimethylhexahydro-s-triazine of the formula

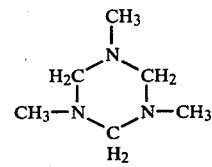

with at least 3 moles of a secondary dialkyl phosphite having branched alkyl radicals to obtain a diester.

2. A process according to claim 1 in which the dialkyl phosphite is diisopropyl phosphite or di-tert.butyl phosphite.

3. A process for the production of methylaminomethylphosphonic acid esters, which comprises heating at a temperature of from about 20° to about 150° C., trimethylhexahydro-s-triazine of the formula

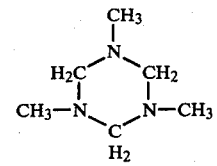

with at least 3 moles of 5,5-dimethyl-[1,3,2]-dioxaphosphorinane of the formula

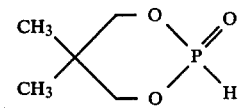

to obtain a diester.

4. A process according to claims 1 or 3 in which the temperature is between 50° and 120° C.

5. A process according to claim 4 in which the temperature is from 100° to 110° C.

* * * * *